US008315706B2

(12) United States Patent
Single

(10) Patent No.: US 8,315,706 B2
(45) Date of Patent: *Nov. 20, 2012

(54) EXTERNAL SPEECH PROCESSOR UNIT FOR AN AUDITORY PROSTHESIS

(75) Inventor: Peter Scott Single, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 404 days.

This patent is subject to a terminal disclaimer.

(21) Appl. No.: 12/435,981

(22) Filed: May 5, 2009

(65) Prior Publication Data

US 2009/0276006 A1   Nov. 5, 2009

Related U.S. Application Data

(63) Continuation of application No. 10/962,441, filed on Oct. 13, 2004, now Pat. No. 7,529,587.

(30) Foreign Application Priority Data

Oct. 13, 2003 (AU) .................................. 2003905570

(51) Int. Cl.
*A61N 1/00* (2006.01)

(52) U.S. Cl. ........................................................ 607/57

(58) Field of Classification Search .............. 607/55–57; 600/25; 381/312
See application file for complete search history.

(56) References Cited

U.S. PATENT DOCUMENTS

| 4,756,312 | A  | 7/1988 | Epley |
| 5,176,620 | A  | 1/1993 | Gilman |
| 5,313,557 | A  | 5/1994 | Osterhout |
| 5,609,616 | A  | 3/1997 | Schulman et al. |
| 6,073,050 | A  | 6/2000 | Griffith |
| 6,711,271 | B2 | 3/2004 | Hou |
| 6,785,397 | B2 | 8/2004 | Arnstein |
| 6,904,156 | B1 | 6/2005 | LeReverend |
| 6,920,226 | B2 | 7/2005 | Sauer |
| 7,346,397 | B2 | 3/2008 | Money et al. |
| 7,529,587 | B2 | 5/2009 | Single |

FOREIGN PATENT DOCUMENTS

| AT | 500375  | 12/2005 |
| WO | 9208330 | 5/1992  |
| WO | 0069512 | 11/2000 |

OTHER PUBLICATIONS

Examiner's First Search Report on Australian Patent Application No. 2004218723, Nov. 7, 2008, 2 pages, Australia.
Austrian Patent Office, "Austrian Search Report," issued in connection with Austrian Patent Application No. A 1134/2005, on Sep. 27, 2005 (1 page).
English language translation of "First Office Action," issued by the Austrian Patent Office in connection with Austrian Patent Application No. A 1134/2005, on Jan. 11, 2010 (1 page).

*Primary Examiner* — Mark W Bockelman
(74) *Attorney, Agent, or Firm* — Kilpatrick, Townsend & Stockton, LLP.

(57) ABSTRACT

A cochlear implant system comprising an external component having an external speech processor unit, and an internal component. The speech processor unit monitors one or more parameters, and the speech processor unit is configured to reduce the power consumption of the cochlear implant system in the absence of one or more parameters.

33 Claims, 4 Drawing Sheets

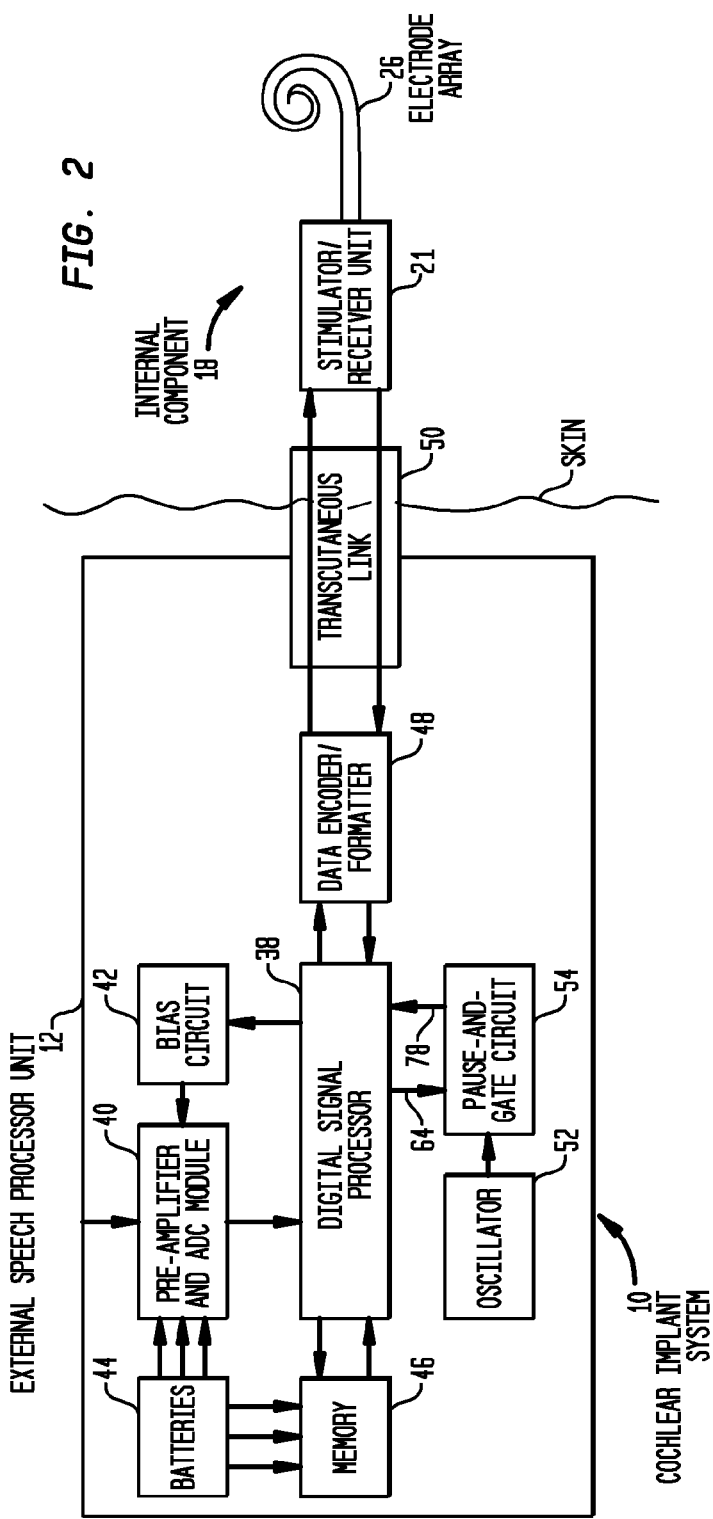

EXTERNAL SPEECH PROCESSOR UNIT FOR AN AUDITORY PROSTHESIS

CROSS-REFERENCE TO RELATED APPLICATIONS

The present application is continuation of co-pending and commonly owned U.S. patent application Ser. No. 10/962,441, filed Oct. 13, 2004, which claims priority from AU Provisional Patent Application No. 2003905570, filed Oct. 13, 2003. The contents of these applications are hereby incorporated by reference herein.

BACKGROUND

1. Field of the Invention

This present invention is generally directed to auditory prosthesis, and more particularly, to an external speech processor unit for an auditory prosthesis.

2. Related Art

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an acoustic hearing aid. Acoustic hearing aids stimulate an individual's cochlea by providing an amplified sound to the cochlea that causes mechanical motion of the cochlear fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from conventional acoustic hearing aids.

It is for this purpose that cochlear implant systems have been developed. Cochlear implants systems, sometimes referred to as cochlear implants herein, bypass the hair cells in the cochlea and directly deliver electrical stimulation signals to the auditory nerve fibres, thereby allowing the brain to perceive a hearing sensation resembling the natural hearing sensation normally delivered to the auditory nerve.

Cochlear implant systems generally consist of two components, an external component, and an internal or implanted component. The internal component receives signals from the external component that are used to provide a sound sensation to a user or recipient of the cochlear implant system, generally and collectively referred to as a recipient herein.

The external component includes a microphone for detecting sounds, such as speech and environmental sounds, a speech processor unit that converts speech into a coded signal, a power source such as a battery, and an external transmitter antenna coil. The speech processor unit outputs a coded signal representing a sound received by the microphone which is transmitted transcutaneously to a stimulator/receiver within the internal component. The stimulator/receiver unit is situated within a recess of the temporal bone of the recipient. This transcutaneous transmission occurs via the external transmitter antenna coil which is positioned to communicate with an implanted receiver antenna coil of the internal component. This transcutaneous transmission link is used to transmit coded signals output by the speech process unit and to provide power to the internal components. The transcutaneous link is, normally, in the form of a radio frequency (RF) link, but other such links have been proposed and implemented with varying degrees of success.

The implanted stimulator/receiver unit includes, in addition to the receiver antenna coil that receives coded signals and power from the external processor component, a stimulator that processes the coded signals. The stimulator outputs electrical stimulation signals to an intracochlea electrode assembly which applies the stimulation signals directly to the auditory nerve, thereby producing a hearing sensation corresponding to the originally detected sound.

The external component is configured to be worn by the recipient. For example, in certain circumstances, the external component may be carried on the body of the user, such as in a pocket of the user's clothing, a belt pouch or in a harness, while the microphone is mounted on a clip mounted behind the ear or on the lapel of the user. More recently, the physical dimensions of the speech processor unit have been able to be reduced allowing for the speech processor unit to be housed in a relatively small unit capable of being worn discreetly behind the ear of the user, sometimes referred to as a Behind-The-Ear (BTE) unit or BTE. In this arrangement, the external transmitter antenna coil is still positioned on the side of the user's head to allow for the transmission of the coded sound signal and power from the sound processor to the implanted stimulator unit.

BTEs have provided a degree of freedom and subtlety for the recipient which has not traditionally been possible with body worn devices. There is no longer a need for extensive cables connecting the body worn processor to the transmitter antenna coil, nor is there a need for a separate microphone unit or battery pack, as the BTE unit contains all the components in one housing. One common feature of all conventional BTE units is the provision of a dedicated mechanical switch for turning the unit on or off. Such a switch is typically small in size and difficult to manipulate, especially in the case of elderly recipients or those who are not very dexterous. Continuous use of the switch causes mechanical fatigue resulting in the switch failing to operate and requiring repair or replacement.

SUMMARY

In one aspect of the present invention, a method of reducing the power consumption of a cochlear implant comprising an external component including a speech processor unit configured to be worn by a recipient, and an internal component is provided. The method comprises: monitoring by the speech processor unit the proximity of the external component unit to the internal component; determining by the speech processor unit that the external component is not in proximity to the internal component; and causing the external component to enter an idle state of reduced power consumption when the speech processor unit determines that the external component is not in proximity to the internal component.

In another aspect of the present invention, a method of reducing the power consumption of a cochlear implant comprising an external component including a speech processor unit configured to be worn by a recipient, and an internal component is provided. The method comprises: monitoring by the speech processor unit motion of the speech processor unit; determining that the speech processor unit is not motion; and causing the external component to enter an idle state of reduced power consumption when the speech processor unit determines that the speech processor unit has ceased movement.

In a still other aspect of the present invention, a cochlear implant is provided. The cochlear implant comprises: an internal component configured to be implanted in a recipient of the cochlear implant; and an external component including a speech processor unit configured to be worn by the recipient, the speech processor unit comprising: a signal processor configured to determine if the external component is in proximity to the internal component, and to place the external component in an idle state of reduced power consumption when the external component is not in proximity to the internal component.

In another aspect of the present invention, a cochlear implant is provided. The cochlear implant comprises: an internal component configured to be implanted in a recipient of the cochlear implant; and an external component including a speech processor unit configured to be worn by the recipient, the speech processor unit comprising: a monitor configured to detect motion of the speech processor unit; and a signal processor configured to place the external component in an idle state of reduced power consumption when the monitor determines that the external component has ceased movement.

BRIEF DESCRIPTION OF THE DRAWINGS

Embodiments of the present invention are described below with reference to the attached drawings, in which:

FIG. 2 is a block diagram of a cochlear implant system, in accordance with the invention, for the implant of FIG. 1;

FIG. 3 is a block diagram of a motion detecting switch, in accordance with embodiments of the present invention;

DETAILED DESCRIPTION

Embodiments of the present invention are generally directed to a cochlear implant comprising an external component including a speech processor unit configured to be worn by a recipient, and an internal component. The speech processor unit is configured to monitor one or more parameters and to reduce the power consumption of the external component when one of the parameters are absent.

More specifically, the speech processor unit monitors one or more parameters that include, for example, the proximity of the external component to the internal component and motion of the speech processor unit. The absence of one or more of these parameters provides an indication that the external component is not being used, for example, due to the recipient being asleep, bathing, etc. As described in greater detail below, if one or more of the parameters are absent, the speech processor unit is configured to reduce the power consumption of the external component. In certain embodiments, the speech processor unit causes the external component to enter an idle state of reduced power consumption.

Figure 1:
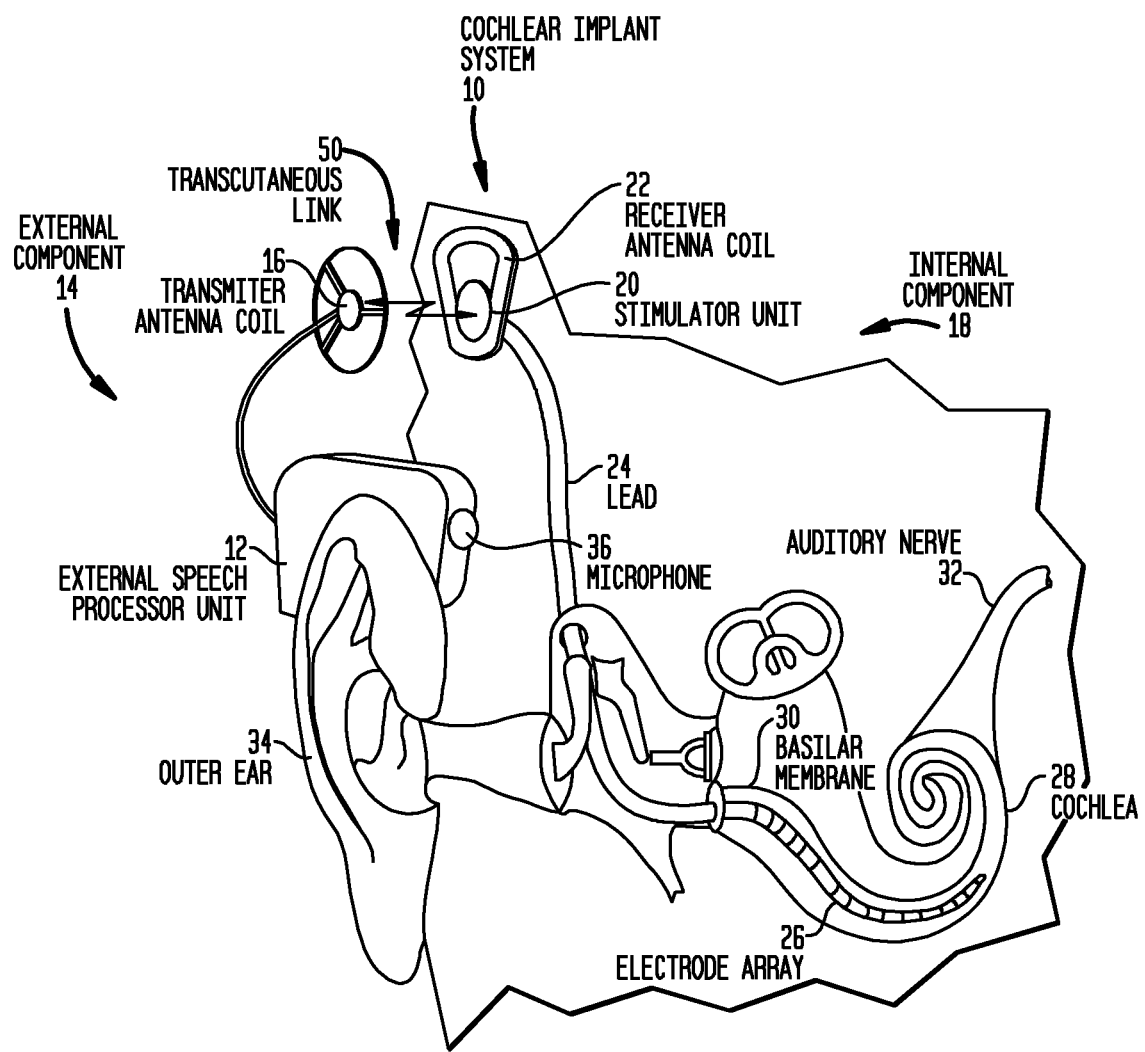
FIG. 1 is a schematic representation of a cochlear implant system, in accordance with an embodiment of the invention.

A cochlear implant system 10 in accordance with embodiments of the present invention is illustrated in FIG. 1. As shown, cochlear implant system 10, sometimes referred to as cochlear implant 10, herein, comprises an external component 14, and an internal component 18 implanted in a recipient. External component 14 includes a microphone 36 for detecting sounds, such as speech and environmental sounds, and an external speech processor unit 12 that converts speech into a coded signal. External component 14 further includes a transmitting device, in the form of a transmitter antenna coil 16.

Internal component 18 includes an implanted receiver and stimulator unit 20 implanted in a recess in a temporal bone of a recipient, and a implanted receiver antenna coil 22. Implanted receiver antenna coil 22 and stimulator unit 20 are sometimes collectively referred to as a stimulator/receiver unit.

Speech processor unit 12 outputs a coded signal representing a sound received by microphone 36 which is transmitted transcutaneously to receiver antenna coil 22 within internal component 18. This transcutaneous transmission occurs via external transmitter antenna coil 116 which is positioned to communicate with receiver antenna coil 22. This transcutaneous transmission link is used to transmit the coded signals output by speech process unit 12 and to provide power to internal component 18. The transcutaneous link is, normally, in the form of a radio frequency (RF) link, but other such links have been proposed and implemented with varying degrees of success.

The coded signals received by receiver antenna coil 22 are provided to stimulator unit 20. The stimulator unit 20 is connected via a conductor or lead 24 to an intracochlea electrode array 26 mounted in the cochlea 28 of the recipient. The received signals are therefore applied by the electrode array 26 to the basilar membrane 30 of the recipient and nerve cells within the cochlea 28 to effect stimulation of the auditory nerve 32 to provide a hearing sensation for the recipient.

In the embodiments of cochlear implant system 10 of FIG. 1, external speech processor unit 12 is configured to be worn behind outer ear 34 of the recipient, and is referred to as a Behind-The-Ear (BTE) unit or simply BTE. That is, speech processor unit 12 has sufficiently small dimensions to be mounted behind outer ear 34. As shown, external speech processor unit 12 has therein or thereon microphone 36.

Embodiments of speech processor unit 12 are described below with reference to FIG. 2. As shown in FIG. 2, speech processor unit 12 comprises a pre-amplifier and ADC module 40. Microphone 36 (FIG. 1) provides auditory inputs pre-amplifier and ADC module 40. Pre-amplifier and ADC module 40 may be implemented as a single module which may normally draw power supplied by a bias circuit 42. The bias circuit may have a power down control operable under the control of the signal processor. Bias circuit 42 has a power-down control. When the power-down control is activated, module 40 ceases operation. When the module 40 ceases operation, it is put in a mode which draws only a relatively minute amount of power.

The auditory inputs are pre-processed by pre-amplifier and ADC module 40, and provided to a signal processor 38 which my comprise a digital signal processor. Data from signal processor 38 is fed to a data encoder/formatter 48. The formatter 48 is used to send stimulation commands and power across a transcutaneous link 50 to stimulator/receiver unit 21 of internal component 18 of cochlear implant system 10. Thus, the formatter may feed signals in the form of stimulation commands, being coded sound signals, and power signals. Transcutaneous link 50 is made up of the transmitter antenna coil 16 of the external component 14 and the receiver antenna coil 22 of the implant 18.

Transcutaneous link 50 may also be used to receive messages from internal component which may be fed back via formatter 48 to signal processor 38. Specifically, signal processor 38 is configured to interrogate internal component 18 and to receive messages back from internal component 18 via formatter 48. When stimulation commands are to be sent by signal processor 38 to internal component 18, the information is encoded by the formatter 48 into a coded signal, being stimulation commands representative of the sound signal received from the microphone 36.

Signal processor 38 analyses received sound signals from the microphone 36. The received sound signals are split up into frequency bands in accordance with the tonotopic arrangement of the electrodes of electrode array 26. Signal processor 38 analyses the amplitude of the signals in each discrete frequency band in accordance with a specific sound processing strategy. For example, signal processor 38 can detect the "n" largest outputs for each filter channel, measure the amplitude of each filter channel and rank them accordingly.

Following frequency analysis and processing of the sound signals, signal processor 38 can access data allocating each frequency band to an electrode pair of electrode array 26 from a memory 46. Memory 46 also contains psychophysical data, such as threshold and comfort levels of the recipient as mapped from each of the electrodes of the electrode array 26. Using the above information, the sound signal is mapped to a recipient's electrode array 26 by selecting the electrodes assigned to the particular frequency and choosing a level between comfort and threshold to represent the loudness of that frequency component.

Also as shown, speech processor unit 12 includes a power source, shown by internal batteries 44, which provides power to the other components of speech processor unit 12. The power provided by batteries 44 is also transcutaneously transmitted to internal component 18. It is a desire of the industry to reduce power consumption of cochlear implant 10 so that the batteries 44 require replacement as infrequently as possible.

Speech processor unit 12 also includes an oscillator 52. Oscillator 52 generates a master clock signal 78 used by all components of speech processor unit 12.

Speech processor unit 12 is, where applicable, made using CMOS circuitry for all digital circuits. In particular, CMOS circuitry is used for signal processor 38, formatter 48 and memory 46. In addition, oscillator 52 is a CMOS design which draws approximately 100 µA or less.

In embodiments of the present invention, oscillator 52 provides its output to a pause-and-gate circuit 54. Pause-and-gate circuit 54 consists of a low-power counter that gates the clock from oscillator 52 to signal processor 38. In a normal operating mode, circuit 54 passes clock signal 78 from oscillator 52 to signal processor 38 and, from there, to the rest of speech processor unit 12. In a pause mode, circuit 54 interrupts clock signal 78 to signal processor 38 and waits for a delay signal from signal processor 38. Signal processor 38 controls when pause-and-gate circuit 54 enters its pause mode.

As noted above, embodiments of the present invention are generally directed to reducing the power consumption of a cochlear implant upon the detection of one or more parameters. In one embodiment of the invention, the parameter monitored by the speech processor unit may be the proximity of the external component to the internal component. In these embodiments, the speech processor unit is configured to continually or periodically determine of the external component is in proximity to the internal component by sending an interrogation signal to determine if the internal component is present. It will be appreciated that, should the external unit have been removed from the recipient's body, normally behind the recipient's ear, the internal component will not be detected by the digital signal processor, and thus the external component is not in proximity to the internal component. This may be taken as an indication that the external component is not being used, for example, due to the recipient being asleep or in a situation where the cochlear implant is not being used, for example, while bathing, etc. As described in greater detail below, if the external component is not in proximity to the internal component, the power consumption of the cochlear implant system may reduced.

In another embodiment of the invention, the parameter monitored by the unit may be motion of the recipient. Thus, the unit may include a motion-detecting means. The motion-detecting means may be in the form of a mercury switch. In the absence of motion, the switch may cause the speech processor unit to reduce the power consumption of the cochlear implant.

In yet a further embodiment of the invention, the parameter being monitored may be a value of reflected impedance as "seen" by the speech processor unit. When the receiver antenna coil has been removed, the reflected impedance as detected by the signal processor may be much higher than when the receiver antenna coil is present. Thus, by appropriate calculation to take into account current drawn during stimulation and the current drawn by the components of the unit itself, the signal processor can determine whether or not the implanted component is present. If not, the signal processor may follow substantially the same procedure as described above with reference to the first embodiment.

Figure 5:
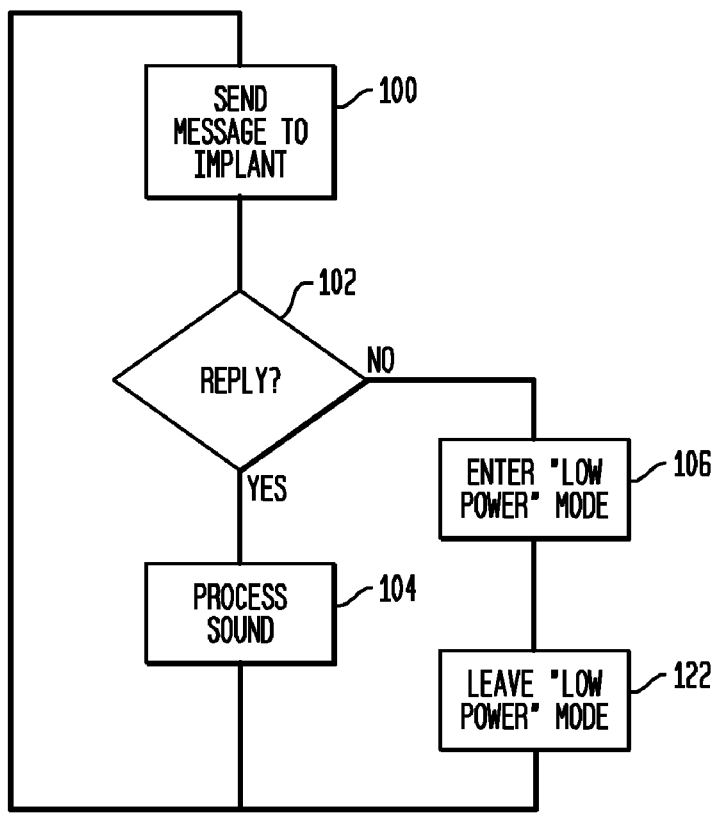
FIG. 5 is a flow chart illustrating the operations performed by the speech processor unit of FIG. 2, in accordance with embodiments of the present invention.
Figure 6:
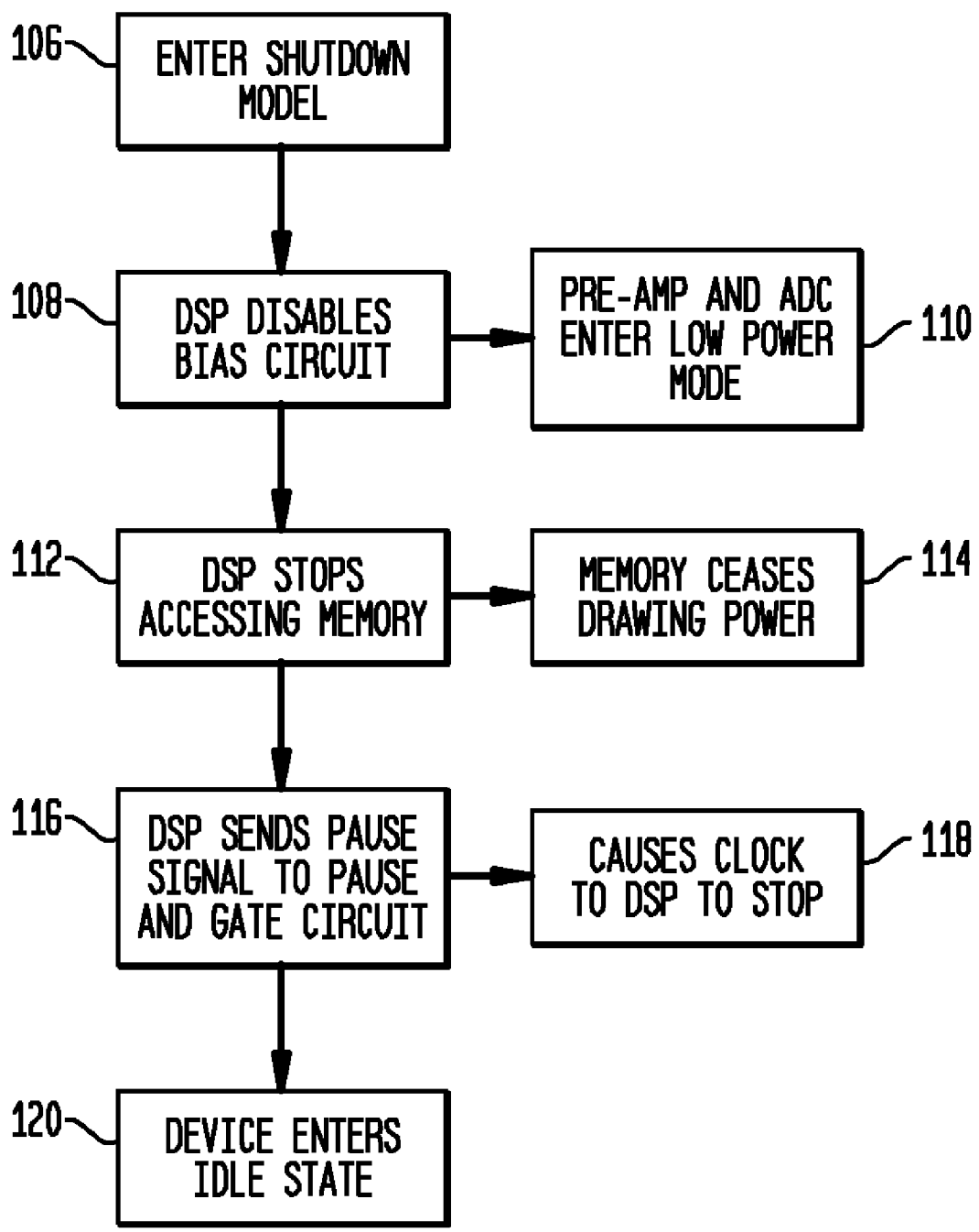
FIG. 6 is a flow chart illustrating the operations performed by a speech processor unit in accordance with embodiments of the present invention.

In certain embodiments of the present invention, external speech processor unit 12 operates as follows to reduce the power consumption of cochlear implant system 10. The operation is described with reference to FIG. 5 and 6. The following discussion assumes that cochlear implant system 10 is operating under normal conditions and is processing sound. All circuits of external speech processor unit 12 are active. Periodically, for example, once every 10 seconds, signal processor 38 polls internal component 18 with a message that includes a telemetry command at step 100 in FIG. 5 and awaits a reply 102. If signal processor 38 receives a response from the internal component 18, it "knows" that the internal component is present and in proximity to external component 14. As such, signal processor 38 continues processing sound 104. If, however, signal processor 38 does not receive a telemetry response, it can send one or more telemetry commands to internal component 18 to detect if its receiving antenna coil 22 is present. After confirming that the receiving antenna coil 22 is not present, speech processor unit 12 assumes that this is because the receiving antenna coil 22 is not in communication with transmitting antenna coil 16 of external component 14. This is taken as a message to "switch off", i.e. to enter an idle state or shutdown mode as shown at step 106 (FIGS. 5 and 6).

Signal processor 38 (or "DSP") then starts its shut-down routine as described with reference to FIG. 6 of the drawings. This routine involves one or steps including, disabling bias circuit 42 at step 108. Disabling the bias circuit 42 causes pre-amplifier and ADC module 40 to enter a low-power state as shown 110. The shutdown routine may also include signal processor 38 disabling or stopping the sending of commands, encoded signals or power to internal component 18, and/or disabling or stopping the accessing of memory 46 by signal processor 38 at step 112. When signal processor 38 stops accessing memory 46, this causes memory 46 to stop drawing power from batteries 44 as shown at 114.

Finally, the shut-down routine may include signal processor 38 sending a "pause" signal, via a pause input 64 (FIGS. 2 and 4) to pause-and-gate circuit 54 at step 116. This causes circuit 54 to enter its pause mode whereby clock signal 78 from oscillator 52 to signal processor 38 is interrupted as shown at 118.

Following the implementation of all of the above steps, all CMOS circuits are in an idle state 120. Oscillator 52 and pause-and-gate circuit 54 continue to draw power from the batteries 44 but no other components do or, more accurately, the power drawn is so small as to be relatively negligible. In this state, the power drawn by speech processor unit 12 is that drawn by oscillator 52 and is typically less than 100 µA.

Speech processor unit 12 remains in the idle state for the delay generated by pause-and-gate circuit 54. A typical value for this delay is of the order of about 1 second. When this delay is completed, clock signal 78 from oscillator 52 to signal processor 38 is re-applied by pause-and-gate circuit 54 to signal processor 38. Signal processor 38 then sends a telemetry command to the internal component 18 as shown at 122 in FIG. 5 of the drawings. Assuming the internal component 18 is still not present (in proximity to external component), signal processor 38 will receive no response. This causes signal processor 38 to instruct pause-and-gate circuit 54 to enter its pause mode once again.

The unit 12 can remain in this mode for any time period ranging from minutes to many hours as long as the transmitter antenna coil 16 is not placed on the recipient's head which would re-establish the transcutaneous link 50 to the implant 18. Thus, if the recipient has placed the transmitter antenna coil 16 in register with the receiver antenna coil 22, the link 50 is re-established. Thus when the signal processor 38 again sends a detection command to internal component 18, it will receive a response. It then knows that it has to start processing sound again. In this configuration, signal processor 38 re-enables pre-amplifier and ADC module 40, waits a short time for any analogue circuitry to stabilise and recommences sound processing.

A typical speech processor unit 12 draws between 2-25 mA when operating. For the sake of the example, it is assumed that the current drawn is 15 mA on average. It is also assumed that it takes 1 ms for the speech processor to re-activate, send a telemetry command, receive a reply and shut down again. Thus, with a signal processor 38 having a 10 MHz clock, this allows 1000 instructions for operation which is well within the capabilities of a standard signal processor 38. In its idle state, unit 12 draws approximately 100 µA. Thus, the average current drawn by speech processor unit 12 is approximately 105 µA. This is sufficiently low that a battery could provide this power for a long period of time. A typical battery has a capacity of 300 mAH. Thus, the processor unit 12 can operate for nearly 3000 hours in this mode.

Figure 4:
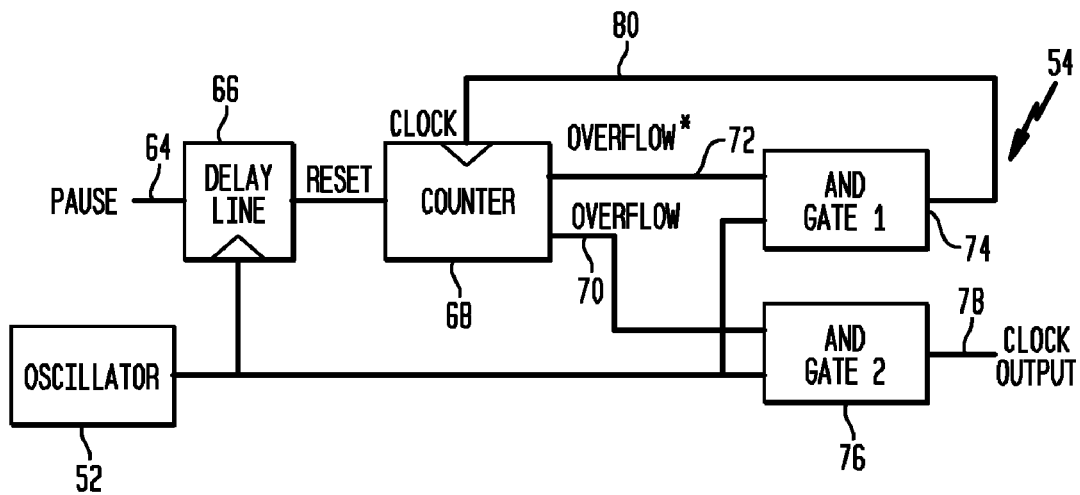
FIG. 4 is a block diagram of the pause-and-gate circuit of FIG. 2. in accordance with embodiments of the present invention.

An implementation of the pause-and-gate circuit 54 is shown in FIG. 4 of the drawings. Circuit 54 has a pause input 64 that, as described above, is asserted by signal processor 38 when it has failed to detect internal component 18 and so initiates the low-power routine. A delay module 66 allows the DSP clock signal 78 to continue while signal processor 38 clears pause input 64 to prevent unit 12 from locking up.

Further, as indicated above, oscillator 52 provides clock signal 78 for the signal processor 38 and a clock signal 80 for a counter 68 of the pause-and-gate circuit 54.

Counter 68 sets the time for the "idle" state for unit 12. Counter 68 has two outputs, an "Overflow" output 70 and an "Overflow*" output 72. The "Overflow" output 70 is asserted when the count has reached its maximum value. The "Overflow*" output 72 is the logical inverse of "Overflow" output 70. An AND gate 74 gates the "Overflow*" output 72 and the oscillator 52 to provide the clock signal 80 for the counter 68. A second AND gate 76 gates the "Overflow" output 70 and the oscillator 52 to provide the clock signal 78 for the signal processor 38.

Circuit 54 operates in the following manner. Under normal operating conditions, when internal component 18 is detected, oscillator 52 is running and the Overflow output 70 is high. This allows clock signal 78 to toggle and drive signal processor 38. The "Overflow*" output 72 is low so the AND gate 74 prevents oscillator 52 clocking counter 68.

To enter the low-power state, signal processor 38 sets the pause signal 64. This initiates a pulse in the delay module 66. Signal processor 38 then resets the pause signal 64. The delay module 66 has as many stages as the number of clock cycles required by signal processor 38 to clear the pause signal 64 to allow the pause signal 64 to be reset.

A pulse from the delay module 66 resets counter 68. Resetting of counter 68 causes the "Overflow" output 70 going low which, in turn, results in clock signal 78 to the signal processor 38 being inhibited by AND gate 76. The "Overflow*" output 72 goes high so oscillator 52 clocks counter 68 via the AND gate 74. Counter 68 has sufficient stages that it can count for the time for which unit 12 must be in its low-power state. At the end of this time, when counter 68 has reached its maximum count value, the "Overflow" output 70 goes high, allowing clock signal 78 to signal processor 38 to resume. The "Overflow*" output 72 goes low blocking the clock signal 80 to the counter 68. Clock signal 78 is then available to signal processor 38, allowing it to check for the presence of the implant 18.

In a variation of the invention, pause-and-gate circuit 54 can be implemented as software in signal processor 38 if signal processor 38 is configured to run a software timer at sufficiently low power.

Further, if signal processor 38 has a set of event counters for timing real-time events, these might be suitable for implementing the pause-and-gate function. These counters generate an interrupt when they have run for the pre-allocated time. The interrupt starts the signal processor 38 running again.

As noted above, the above described embodiments of the present invention illustrate implementations in which cochlear implant system 10 enters a reduced power state when the external component is not in proximity to the internal component. In another embodiment of the invention, illustrated in FIG. 3 of the drawings, speech processor unit 12 includes a motion detecting mechanism in the form of a motion detecting switch 56. The motion detecting switch 56 is connected to the pause-and-gate circuit 54. In the absence of motion for a predetermined period of time, switch 56 causes the pause-and-gate circuit 54 to enter its pause mode interrupting clock signal 78 from the oscillator 52 to the signal processor 38. This causes unit 12 to enter its idle state, as described above. It would be appreciated that any of the above described methods for reducing power may be used together or individually to reduce the power consumption of the cochlear implant system 10 in the absence of motion or when the external component is not in proximity to the internal component.

Conveniently motion switch 56 is a mercury switch having a pair of contacts 58 which, when switch 56 is closed, is bridged by a blob of mercury 60. Contacts 58 and mercury 60 are housed in an envelope 62 of a non-conductive material, such as glass. The switch 56 is arranged so that, in the absence of motion, mercury 60 does not bridge contacts 58, thereby disabling switch 56. Movement of the recipient is required to move mercury 60 so that it bridges contacts 58. When this occurs, pause-and-gate circuit 54 enters it normal mode.

Thus, as long as the external component 14 of the implant 12 is left idle, for example, on a bedside table during the night while the recipient is a sleep, speech processor unit 12 will remain in its idle mode. If the unit 12 is, for example, bumped then the signal processor 38 will be activated, but may further detect that internal component 18 is absent and the unit 12 will again be placed in its idle state.

Yet a further embodiment of the invention relies on reflected impedance. In this embodiment of the invention, the reflected impedance of implant receiver antenna coil 22 affects the input impedance of transmitter antenna coil 16 as detected by signal processor 38. This embodiment operates in a similar manner to the implementation described above with reference to FIG. 2 of the drawings except that signal processor 38 measures current used to drive the implant 18.

For this embodiment of the invention, battery 44 has a small resistor in series forming an ammeter so that signal processor 38 can measure the supply current.

Since the supply current of the speech processor unit 12 varies with the stimulation rate, signal processor 38 must compensate for the rate at which it is sending radio frequency (RF) signals across the link 50 the implant 18. For this purpose the signal processor performs the following steps:

records the rate at which it sends RF frames to the implant 18;
measures the current drawn from the battery 44 using the ammeter;
subtracts from the values measured, the current drawn by the signal processor 38 itself, the analogue circuitry etc.;
from the previous step, calculates the power drawn from the battery 44 for each stimulation;
from the calculation in the preceding step, determines whether or not the implant 18 is present.

Typically, when signal processor 38 is driving internal component 18 it draws a current of about 12 mA maximum. When receiver coil 22 is absent, the drawn current can reach levels of up to 80 mA. As a result, this large difference in values means that errors from the ammeter or from the calculation are not critical.

Accordingly, it is an advantage of the invention that a cochlear implant system 10 is provided which omits a mechanical on/off switch in the external processor. Such a mechanical switch is prone to failure as it is used many times by the recipient. In addition, because of the small size of behind the ear external speech processor units 12, the switch itself is also of small dimensions. This makes it difficult for older people or less dexterous people to manipulate such switches. Because the invention obviates the need for a switch, this problem is also overcome.

In addition, one of the causes of failures of external speech processor units 12 is the ingress of moisture. Often the ingress of moisture is through the aperture in a casing of the external speech processor unit for a lever of an on/off switch. Once again, because the on/off switch is able to be eliminated in the present invention, this problem is also, to at least a large extent, overcome. Thus, this renders the system 10 more versatile as it is now possible for recipients to use the system 10 even in wet environments such as when showering or out in the open and being caught in the rain.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of reducing the power consumption of an auditory prosthesis comprising an external component including a speech processor unit configured to be worn by a recipient, and an internal component, the method comprising:
   monitoring by the speech processor unit the proximity of the external component unit to the internal component;
   determining by the speech processor unit that the external component is not in proximity to the internal component; and
   causing the external component to enter an idle state of reduced power consumption when the speech processor unit determines that the external component is not in proximity to the internal component.

2. The method of claim 1, wherein the speech processor unit comprises a pre-amplifier and ADC module that receives auditory inputs from a microphone, and wherein causing the external component to enter an idle state of reduced power consumption comprises:
   causing the preamplifier and ADC module to enter a low power state.

3. The method of claim 2, wherein the speech processor unit further comprises a bias circuit to control the operation of the pre-amplifier and ADC module, and wherein causing the preamplifier and ADC module to enter a low power state comprises:
   disabling the bias circuit.

4. The method of claim 1, wherein the external component transmits signals to the internal component, and wherein causing the external component to enter an idle state of reduced power consumption comprises:
   disabling the transmission of signals from the external component to the internal component.

5. The method of claim 1, wherein the speech processor unit comprises a memory, and wherein causing the external component to enter an idle state of reduced power consumption comprises:
   disabling the draw of power by the memory.

6. The method of claim 5, wherein the speech processor unit comprises a signal processor that accesses the memory, and wherein disabling the draw of power by the memory comprises:
   disabling the access of memory by the signal processor.

7. The method of claim 1, wherein the speech processor unit further comprises a signal processor and an oscillator providing a clock signal to the elements of the speech processor unit, and wherein causing the external component to enter an idle state of reduced power consumption comprises:
   interrupting the clock signal from the oscillator to the signal processor causing clock dependent elements to enter a non-power consuming idle state for a period of time.

8. The method of claim 7, wherein the speech processor unit further comprises a pause-and-gate circuit, and wherein interrupting the clock signal from the oscillator to the signal processor comprises:
sending a pause signal from the signal processor to the pause-and-gate circuit.

9. A method of reducing the power consumption of an auditory prosthesis comprising an external component including a speech processor unit configured to be worn by a recipient, and an internal component, the method comprising:
monitoring by the speech processor unit motion of the speech processor unit;
determining that the speech processor unit is not motion; and
causing the external component to enter an idle state of reduced power consumption when the speech processor unit determines that the speech processor unit has ceased movement.

10. The method of claim 9, wherein the speech processor unit comprises a pre-amplifier and ADC module that receives auditory inputs from a microphone, and wherein causing the external component to enter an idle state of reduced power consumption comprises:
causing the preamplifier and ADC module to enter a low power state.

11. The method of claim 10, wherein the speech processor unit further comprises a bias circuit to control the operation of the pre-amplifier and ADC module, and wherein causing the preamplifier and ADC module to enter a low power state comprises:
disabling the bias circuit.

12. The method of claim 9, wherein the external component transmits signals to the internal component, and wherein causing the external component to enter an idle state of reduced power consumption comprises:
disabling the transmission of signals from the external component to the internal component.

13. The method of claim 9, wherein the speech processor unit comprises a memory, and wherein causing the external component to enter an idle state of reduced power consumption comprises:
disabling the draw of power by the memory.

14. The method of claim 13, wherein the speech processor unit comprises a signal processor that accesses the memory, and wherein disabling the draw of power by the memory comprises:
disabling the access of memory by the signal processor.

15. The method of claim 9, wherein the speech processor unit further comprises a signal processor and an oscillator providing a clock signal to the elements of the speech processor unit, and wherein causing the external component to enter an idle state of reduced power consumption comprises:
interrupting the clock signal from the oscillator to the signal processor causing clock dependent elements to enter a non-power consuming idle state for a period of time.

16. The method of claim 15, wherein the speech processor unit further comprises a pause-and-gate circuit, and wherein interrupting the clock signal from the oscillator to the signal processor comprises:
sending a pause signal from the signal processor to the pause-and-gate circuit.

17. An auditory prosthesis comprising:
an internal component configured to be implanted in a recipient of the auditory prosthesis; and
an external component including a speech processor unit configured to be worn by the recipient, the speech processor unit comprising:
a signal processor configured to determine if the external component is in proximity to the internal component, and to place the external component in an idle state of reduced power consumption when the external component is not in proximity to the internal component.

18. The auditory prosthesis of claim 17, wherein the external component further comprises a transmitter configured to transmit a telemetry command to the internal component, and wherein the signal processor is configured to determine if the external component is in proximity to the internal component based on the response by the internal component to the telemetry command.

19. The auditory prosthesis of claim 18, wherein in the absence of a response by the internal component to the telemetry command the signal processor is configured to determine that the external component is not in proximity to the internal component.

20. The auditory prosthesis of claim 17, wherein the signal processor is configured to determine if the external component is in proximity to the internal component by measuring the impedance between the signal processor and the internal component.

21. The auditory prosthesis of claim 17, wherein the external component further comprises:
a pre-amplifier and an analog-to-digital converter (ADC) module configured pre-process auditory inputs from a microphone; and
a bias circuit configured to control the supply of power to the pre-amplifier and ADC module,
wherein the signal processor is configured to place the external component into the idle state by disabling the supply of power from the bias circuit to the module.

22. The auditory prosthesis of claim 17, wherein the external component is configured to transmit signals to the internal component, and wherein the signal processor is configured to place the external component into the idle state by disabling the transmission of the signals from the external component to the internal component.

23. The auditory prosthesis of claim 17, wherein the external component further comprises:
a battery supply for supplying power to one or more components of the external component, and
wherein the signal processor is configured to place the external component into the idle state by disabling the supply of power from the battery supply to the one or more components.

24. The auditory prosthesis of claim 17, wherein the external component further comprises:
a memory configured to store psychophysical data of a recipient of the auditory prosthesis, and wherein the signal processor is configured to place the external component into the idle state by disabling access to the memory.

25. The auditory prosthesis of claim 17, wherein the external component further comprises:
a controller operable under the control of the signal processor; and
an oscillator configured to deliver a clock signal to the signal processor,
wherein the signal processor is configured to send a pause signal to the controller so as to interrupt the clock signal from the oscillator to the signal processor when the signal processor determines that the external component is not in proximity to the internal component.

26. An auditory prosthesis comprising:
- an internal component configured to be implanted in a recipient of the auditory prosthesis; and
- an external component including a speech processor unit configured to be worn by the recipient, the speech processor unit comprising:
  - a monitor configured to detect motion of the speech processor unit; and
  - a signal processor configured to place the external component in an idle state of reduced power consumption when the monitor determines that the external component has ceased movement.

27. The auditory prosthesis of claim 26, wherein the monitor comprises a mercury switch.

28. The auditory prosthesis of claim 26, wherein the signal processor is configured to place the external component in an idle state of reduced power consumption after the speech processor has ceased movement for a period of time.

29. The auditory prosthesis of claim 26, wherein the external component further comprises:
- a pre-amplifier and an analog-to-digital converter (ADC) module configured pre-process auditory inputs from a microphone; and
- a bias circuit configured to control the supply of power to the pre-amplifier and ADC module,
- wherein the signal processor is configured to place the external component into the idle state by disabling the supply of power from the bias circuit to the module.

30. The auditory prosthesis of claim 26, wherein the external component is configured to transmit signals to the internal component, and wherein the signal processor is configured to place the external component into the idle state by disabling the transmission of the signals from the external component to the internal component.

31. The auditory prosthesis of claim 26, wherein the external component further comprises:
- a battery supply for supplying power to one or more components of the external component, and
- wherein the signal processor is configured to place the external component into the idle state by disabling the supply of power from the battery supply to the one or more components.

32. The auditory prosthesis of claim 26, wherein the external component further comprises:
- a memory configured to store psychophysical data of a recipient of the auditory prosthesis, and wherein the signal processor is configured to place the external component into the idle state by disabling access to the memory.

33. The auditory prosthesis of claim 26, wherein the external component further comprises:
- a controller operable under the control of the signal processor; and
- an oscillator configured to deliver a clock signal to the signal processor,
- wherein the signal processor is configured to send a pause signal to the controller so as to interrupt the clock signal from the oscillator to the signal processor when the monitor determines that the external component has ceased movement.

\* \* \* \* \*